(12) United States Patent
Eaton et al.

(10) Patent No.: US 6,228,032 B1
(45) Date of Patent: *May 8, 2001

(54) STEERING MECHANISM AND STEERING LINE FOR A CATHETER-MOUNTED ULTRASONIC TRANSDUCER

(75) Inventors: John W. Eaton, Palo Alto; David J. Rosa, San Jose; Vaughn Marian, Saratoga; Jay Plugge, Sunnyvale, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,467

(22) Filed: May 25, 1999

Related U.S. Application Data

(63) Continuation of application No. 08/959,493, filed on Oct. 28, 1997, now Pat. No. 5,938,616, which is a continuation of application No. 08/791,598, filed on Jan. 31, 1997, now Pat. No. 5,846,205, which is a continuation of application No. 08/792,897, filed on Jan. 31, 1997, now Pat. No. 5,954,654.

(51) Int. Cl.⁷ ........................................................ A61B 8/12
(52) U.S. Cl. ............................................. 600/463; 600/466
(58) Field of Search ..................... 600/459–463, 600/439, 446; 607/122

(56) References Cited

U.S. PATENT DOCUMENTS

| | | |
|---|---|---|
| 3,938,502 * | 2/1976 | Bom ...................................... 600/463 |
| 4,191,193 | 3/1980 | Seo . |
| 4,207,873 | 6/1980 | Kruy . |
| 4,435,614 | 3/1984 | McAusland . |
| 4,474,174 | 10/1984 | Petruzzi . |
| 4,605,009 | 8/1986 | Pourcelot et al. . |
| 4,794,931 | 1/1989 | Yock . |
| 4,809,704 | 3/1989 | Sogawa et al. . |
| 4,841,976 | 6/1989 | Packard et al. . |
| 4,841,977 | 6/1989 | Griffith et al. . |
| 4,917,097 | 4/1990 | Proudian et al. . |
| 4,947,852 | 8/1990 | Nassi et al. . |
| 4,951,677 | 8/1990 | Crowley et al. . |
| 5,054,492 * | 10/1991 | Scribner et al. ...................... 600/463 |
| 5,199,437 * | 4/1993 | Langberg ............................. 600/463 |
| 5,207,225 | 5/1993 | Oaks et al. . |
| 5,240,003 | 8/1993 | Lancee et al. . |
| 5,275,151 | 1/1994 | Shockey et al. . |
| 5,291,893 | 3/1994 | Slayton . |
| 5,297,553 | 3/1994 | Sliwa, Jr. et al. . |
| 5,305,756 | 4/1994 | Entrekin et al. . |
| 5,322,064 | 6/1994 | Lundquist . |

(List continued on next page.)

OTHER PUBLICATIONS

Seward, J.B., D.L. Packer, R.C. Chan, M.G. Curley, A.J. Tajik (Jul. 1996), "Ultrasound Cardioscopy: Embarking on a New Journey," Mayo Clinic Proceedings, 71(7):629–635.

Wells, *Biomedical Ultrasonics*, Academic Press 1977, pp. 38–42.

*Primary Examiner*—Francis J. Jaworski
(74) *Attorney, Agent, or Firm*—Brinks Hofer Gilson & Lione

(57) ABSTRACT

An ultrasonic transducer includes an elongated catheter that carries a phased linear array of ultrasonic transducer elements at a distal end. This array is aligned with the azimuthal axis of the array oriented substantially parallel to a longitudinal axis of the catheter near the distal end. Two sets of steering lines are carried by the catheter and coupled to the catheter near the distal end. The first set of steering lines is effective to steer the distal end in a first plane, and the second set of steering lines is effective to steer the distal end in a second plane, transverse to the first plane.

9 Claims, 5 Drawing Sheets

U.S. PATENT DOCUMENTS

| | | |
|---|---|---|
| 5,325,860 | 7/1994 | Seward et al. . |
| 5,336,182 | 8/1994 | Lundquist et al. . |
| 5,345,940 | 9/1994 | Seward et al. . |
| 5,351,692 | 10/1994 | Don et al. . |
| 5,359,994 | 11/1994 | Krauter et al. . |
| 5,364,352 | 11/1994 | Cimino et al. . |
| 5,368,037 | 11/1994 | Eberle et al. . |
| 5,375,602 | 12/1994 | Lancee et al. . |
| 5,383,852 | 1/1995 | Stevens-Wright . |
| 5,383,923 | 1/1995 | Webster, Jr. . |
| 5,385,148 * | 1/1995 | Lesh et al. ............................ 600/471 |
| 5,395,327 | 3/1995 | Lundquist et al. . |
| 5,395,329 | 3/1995 | Fleischhackor et al. . |
| 5,397,304 | 3/1995 | Truckai . |
| 5,398,689 | 3/1995 | Connor et al. . |
| 5,400,785 | 3/1995 | Crowley . |
| 5,402,793 | 4/1995 | Gruner et al. . |
| 5,413,107 | 5/1995 | Oakley et al. . |
| 5,417,219 | 5/1995 | Takamizawa et al. . |
| 5,431,168 | 7/1995 | Webster, Jr. . |
| 5,439,006 | 8/1995 | Brennen et al. . |
| 5,453,575 | 9/1995 | O'Donnell et al. . |
| 5,456,258 | 10/1995 | Kondo et al. . |
| 5,462,527 | 10/1995 | Stevens-Wright et al. . |
| 5,476,107 | 12/1995 | Oakley et al. . |
| 5,479,930 | 1/1996 | Gruner et al. . |
| 5,489,270 | 2/1996 | van Erp . |
| 5,492,126 | 2/1996 | Hennige et al. . |
| 5,512,035 | 4/1996 | Konstorum et al. . |
| 5,514,115 | 5/1996 | Frantzen et al. . |
| 5,527,279 | 6/1996 | Imran . |
| 5,531,685 | 7/1996 | Hemmer et al. . |
| 5,562,096 | 10/1996 | Hossack et al. . |
| 5,571,085 | 11/1996 | Accisano, III . |
| 5,662,606 | 9/1997 | Cimino et al. . |
| 5,699,805 | 12/1997 | Seward et al. . |
| 5,704,361 | 1/1998 | Seward et al. . |
| 5,713,363 | 2/1998 | Seward et al. . |
| 5,722,402 | 3/1998 | Swanson et al. . |
| 5,846,205 * | 12/1998 | Curley et al. ......................... 600/472 |
| 5,865,801 | 2/1999 | Houser . |
| 5,876,345 * | 3/1999 | Eaton et al. ......................... 600/466 |
| 5,938,616 * | 8/1999 | Eaton et al. ......................... 600/463 |
| 5,954,654 * | 9/1999 | Eaton et al. ......................... 600/462 |

* cited by examiner

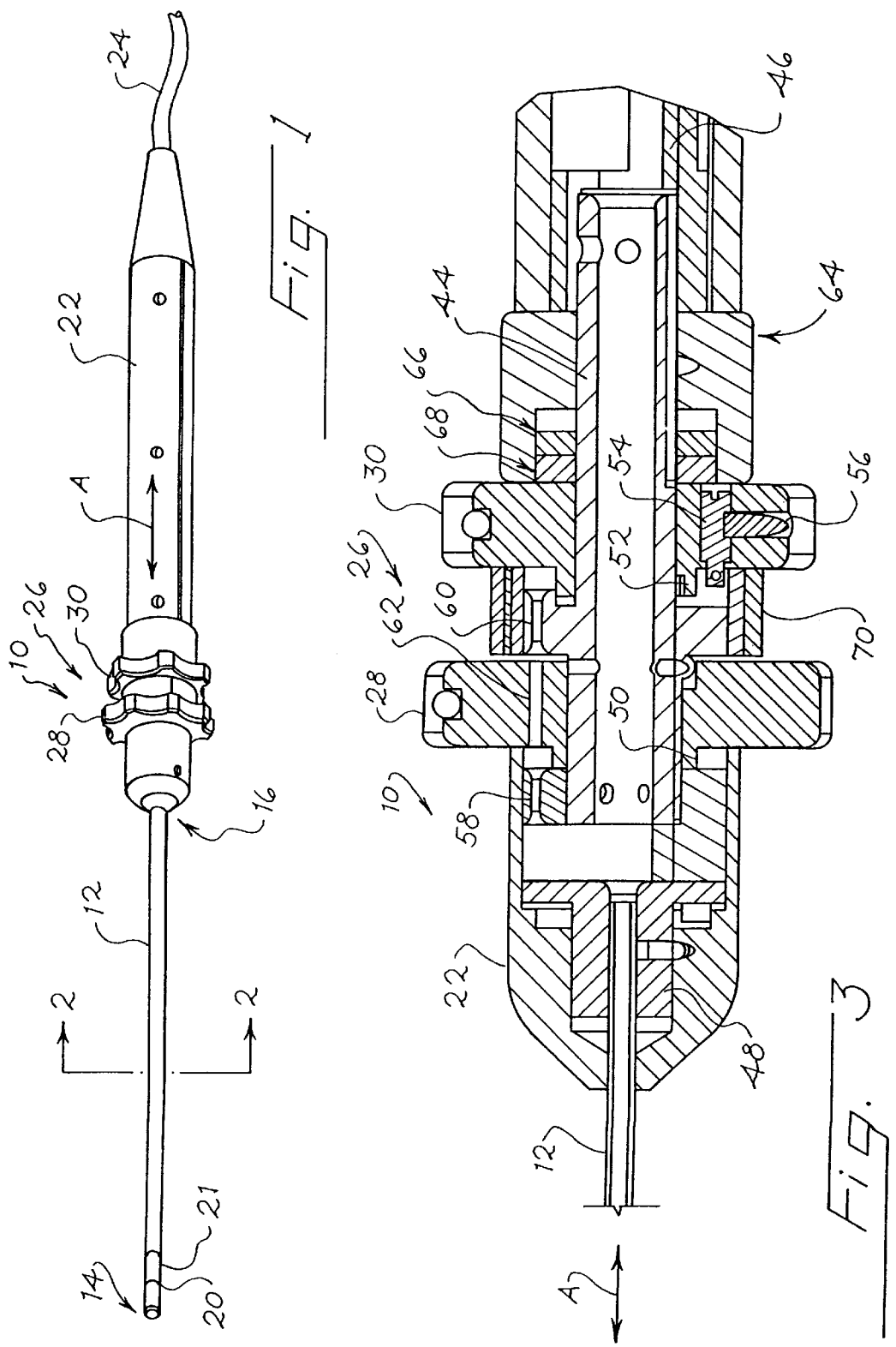

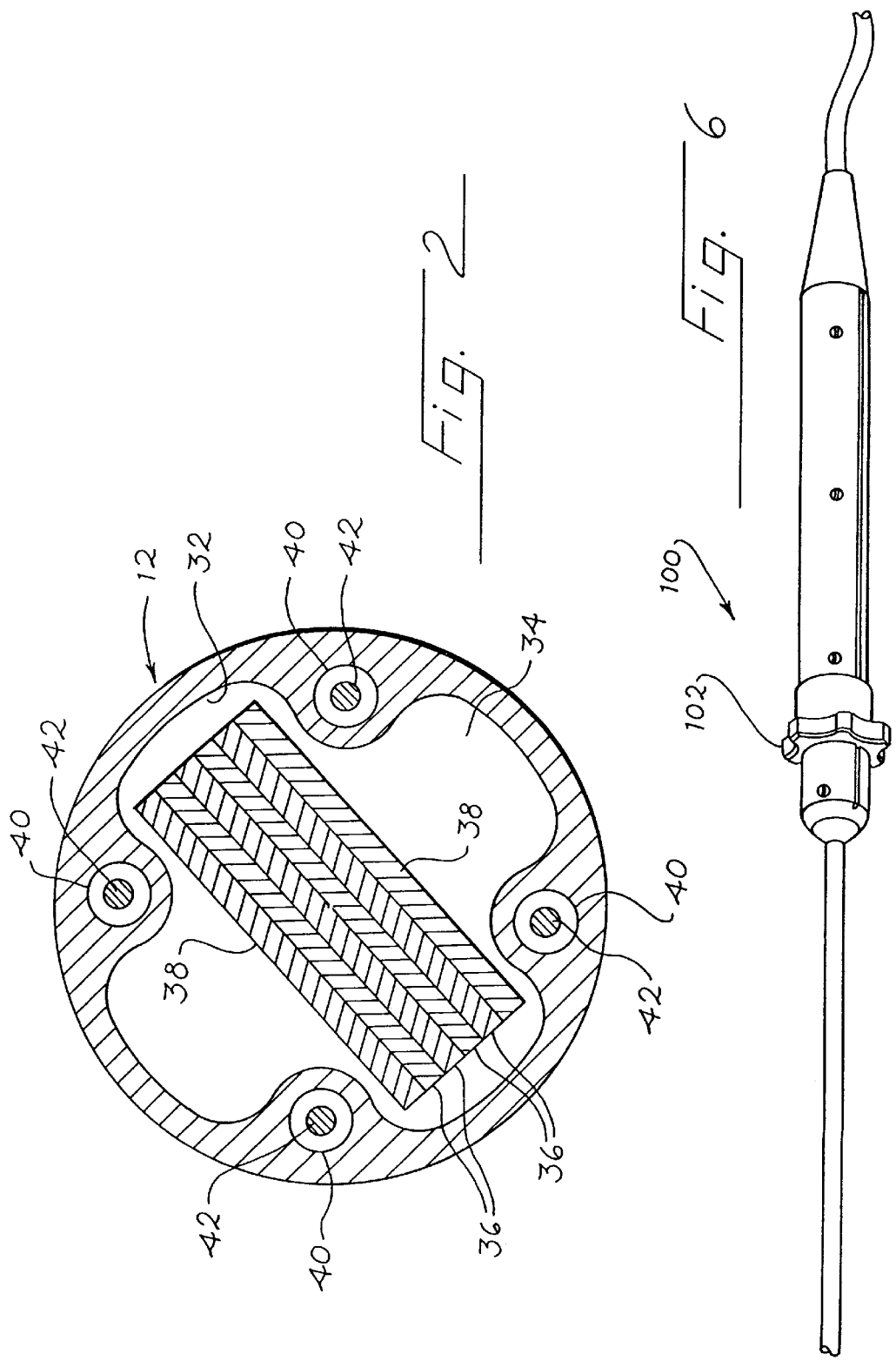

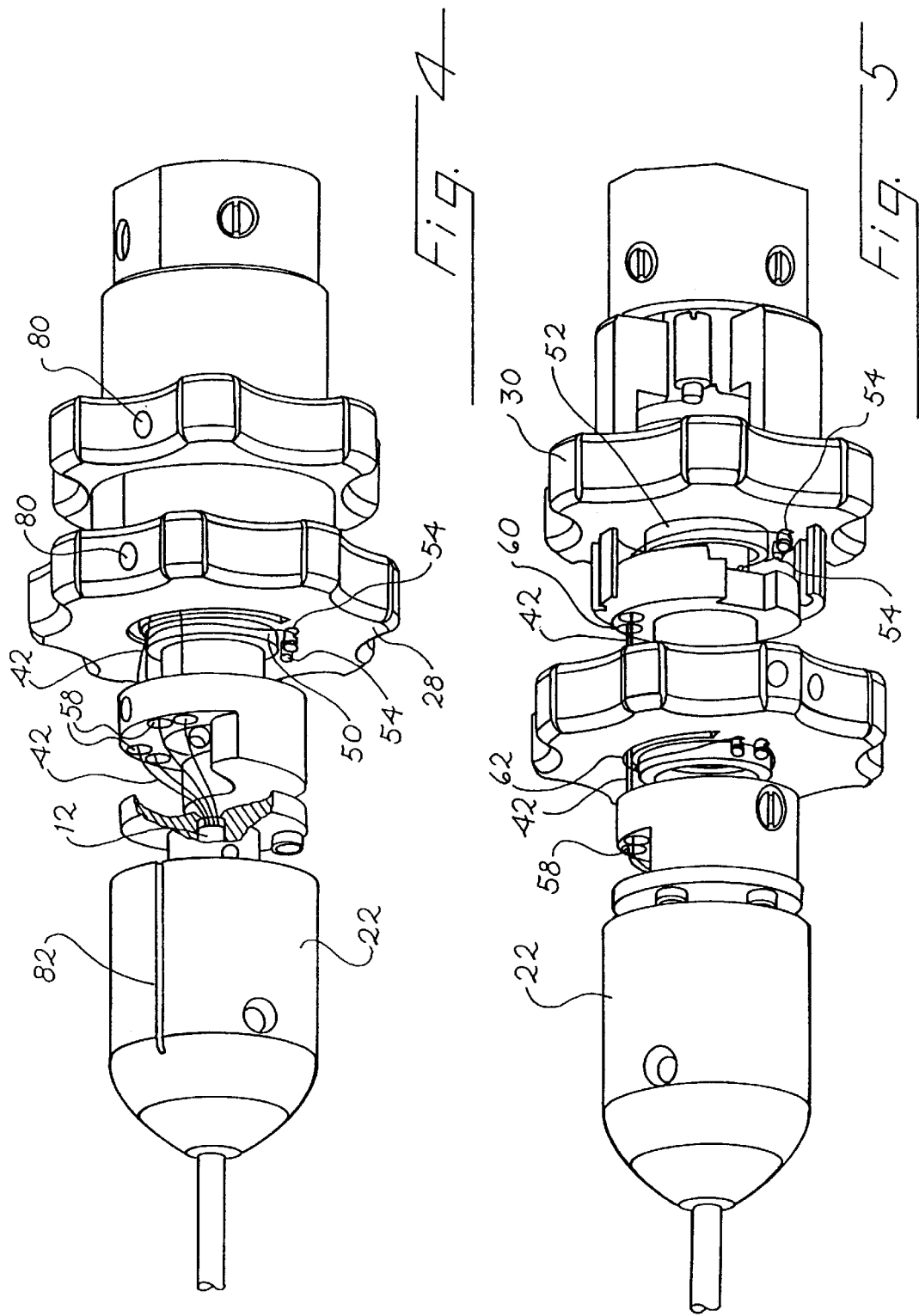

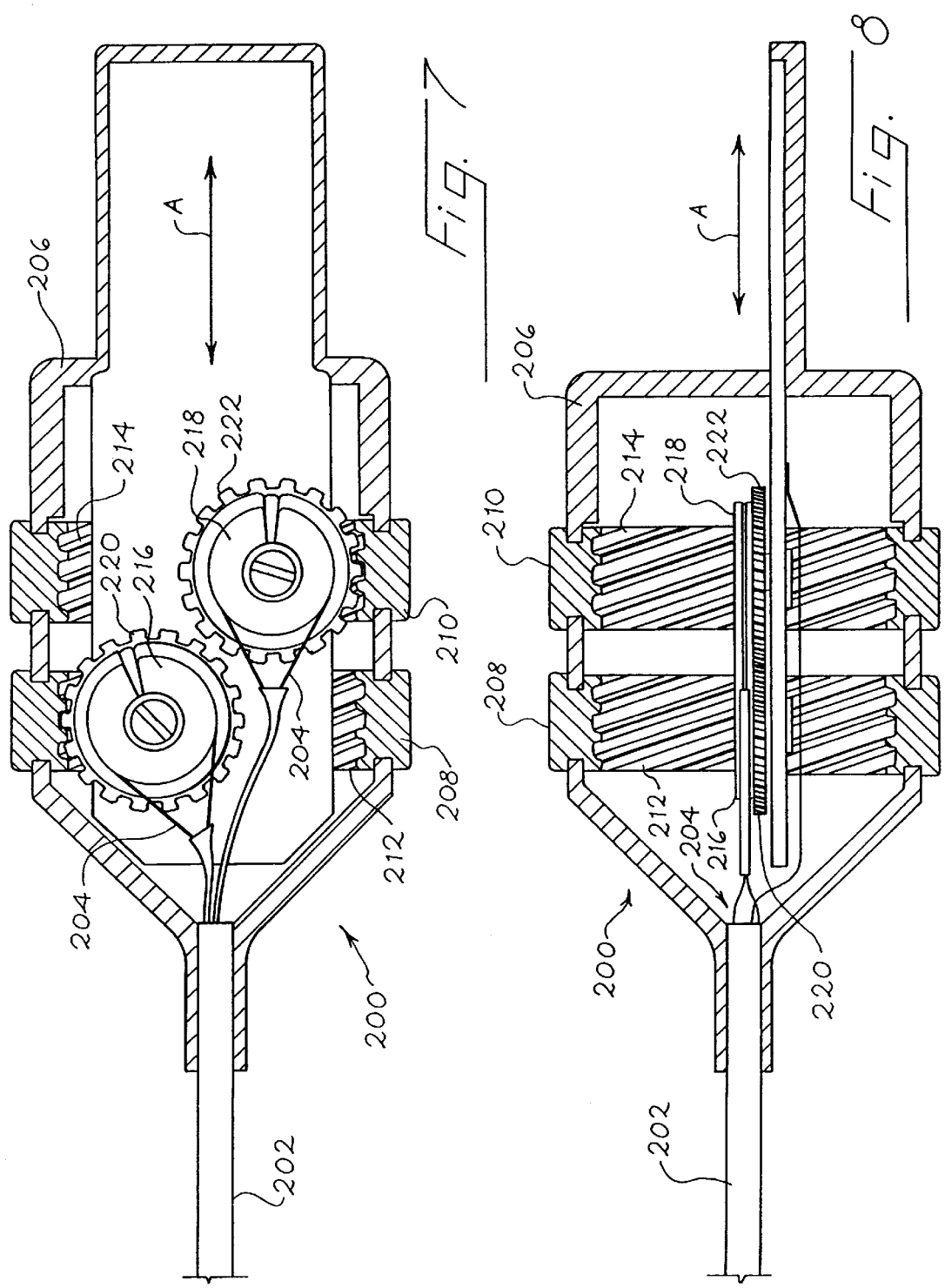

STEERING MECHANISM AND STEERING LINE FOR A CATHETER-MOUNTED ULTRASONIC TRANSDUCER

CROSS REFERENCE TO RELATED APPLICATIONS

This application is a continuation of U.S. patent application Ser. No. 08/959,493, filed Oct. 28, 1997 and now U.S. Pat. No. 5,938,616; which is a continuation of U.S. patent applications Ser. Nos. 08/791,598 (now U.S. Pat. No. 5,846, 205) and 08/792,897 now U.S. Pat. No. 5,954,654, both filed Jan. 31, 1997.

BACKGROUND OF THE INVENTION

This invention relates to catheter-mounted ultrasonic transducers.

Catheter-mounted ultrasonic transducers are known to the art, as described for example in U.S. Pat. No. 4,794,931 and 5,368,037. These catheter-mounted transducers are single use, disposable devices which provide a radial image format either by means of a radial phased array or a rotating crystal. These devices do not include any mechanism for steering or articulating the tip of the catheter. Because the catheter tip cannot be steered, it is in general not possible to position the transducer optimally to obtain different views of the tissue or structure being imaged.

Catheters other than ultrasonic imaging catheters currently exist which have articulating tips. One typical steering mechanism for such a catheter uses a knob which rotates about an axis perpendicular to the length of the catheter. As the user rotates the knob clockwise or counterclockwise, the tip of the catheter will articulate either up and down, or left and right. In addition to manipulating the catheter tip with the knob, the catheter is generally rotated within the vessel by rotating the control housing. Such rotation of the control housing causes the knob to rotate as well as the catheter, and can place the knob in an relatively inaccessible position for the user. Awkward positioning of the steering knob can make manipulating the catheter tip difficult.

Accisano U.S. Pat. No 5,571,085 and Fleischhackor U.S. Pat. No. 5,395,329 disclose control handles for steerable catheters which utilize a rotating collar to move a slide longitudinally in the catheter handle. Steering lines are connected to the slide such that reciprocation of the slide steers the distal tip of the catheter. This arrangement provides the advantage of a steering actuator which extends around the complete circumference of the handle and rotates about the longitudinal axis of the handle.

SUMMARY OF THE INVENTION

The preferred embodiment described below is an ultrasonic transducer that includes an elongated catheter having a distal end portion and a proximal end portion, and an array of transducer elements carried by the catheter adjacent the distal end portion. This array comprises an azimuthal axis oriented substantially parallel to a longitudinal axis of the catheter adjacent the distal end portion. The catheter carries first and second sets of steering lines that are coupled to the catheter near the distal end portion. The first set of steering lines is effective to steer the distal end portion in a first plane, and the second set of steering lines is effective to steer the distal end portion in a second plane, different than the first plane.

BRIEF DESCRIPTION OF THE DRAWINGS

FIG. 1 is a perspective view of a catheter-mounted ultrasonic transducer assembly that comprises the first preferred embodiment of this invention.

FIG. 2 is a cross-sectional view taken along line 2—2 of FIG. 1.

FIG. 3 is a cross-sectional view of a portion of the handle of the embodiment of FIG. 1.

FIGS. 4 and 5 are two exploded, perspective views of the embodiment of FIG. 1.

FIG. 6 is a side view of a second preferred embodiment of this invention.

FIG. 7 is a longitudinal sectional view of a third preferred embodiment of this invention.

FIG. 8 is a longitudinal sectional view of the embodiment of FIG. 7, taken in a plane perpendicular to that of FIG. 7.

DETAILED DESCRIPTION OF THE PRESENTLY PREFERRED EMBODIMENTS

Figure 9:
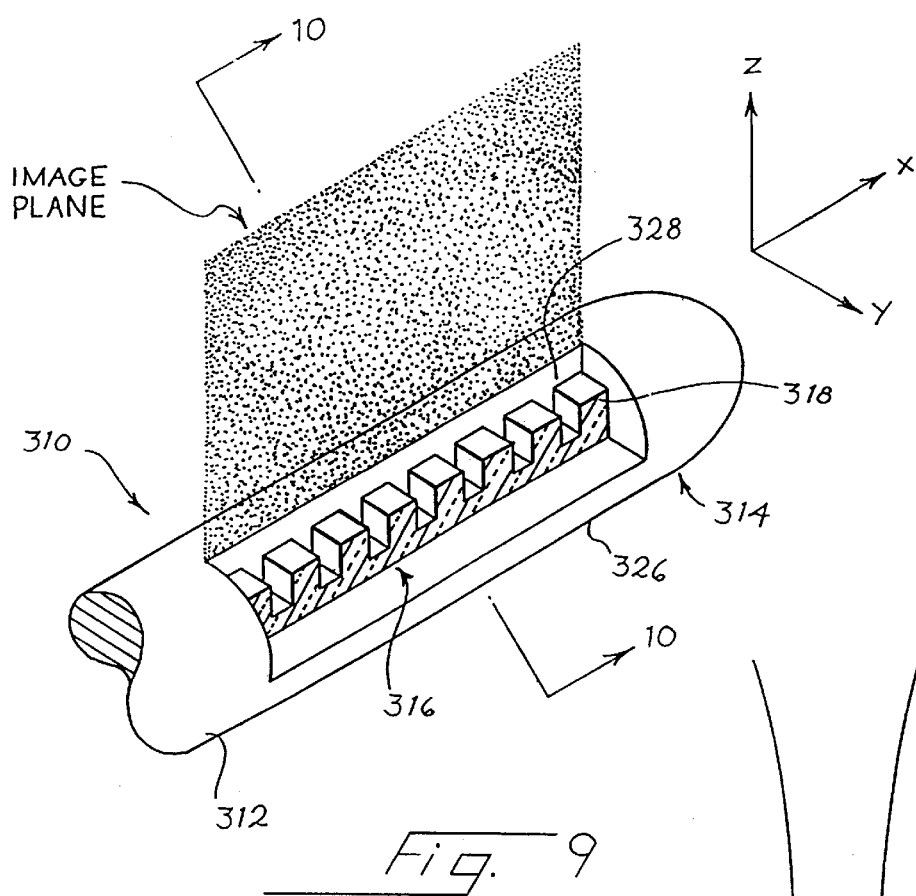
FIG. 9 is a perspective view in partial cutaway of a catheter mounted transducer of a transducer assembly suitable for use with this invention.

Turning now to the drawings, FIG. 1 shows a side view of a transducer assembly 10 that incorporates a preferred embodiment of this invention. The transducer assembly 10 includes an elongated catheter 12 having a distal end 14 and a proximal end 16. A linear array of transducer elements 20 is carried by the distal end 14 of the catheter 12. The transducer elements 20 can be arranged in a linear or a curvilinear phased array, depending upon the application. The portion of the catheter 12 immediately proximal to the transducer elements 20 is formed of a lower hardness polymer enabling it to articulate or steer in any of four directions (up/down and left/right).

The catheter 12 is mounted in a housing 22 that is connected by a cable 24 to a medical diagnostic ultrasonic imaging system (not shown). The housing 22 includes a steering mechanism 26 that in turn includes first and second actuators, which in this embodiment take the form of steering rings 28,30. The first steering ring 28, when rotated, causes the distal end 14 to move in a first plane, and the second steering ring 30, when rotated, causes the distal end 14 to articulate in a second plane, transverse to the first plane. As shown in FIG. 1, the first and second steering rings 28,30 extend circumferentially around the housing 22, and each pivots about an axis A which is parallel to the centerline of the catheter 12 adjacent the proximal end 16.

Turning now to FIG. 2, the catheter 12 includes a conduit 32 that defines a central lumen 34. The central lumen 34 carries a stack of flexible circuit strips 36, 38. The flexible circuit strips 36 carry transmit signals to the transducer elements and receive signals from the transducer elements. The flexible circuit strips also include ground return paths. The flexible circuit strips 38 are provided with uninterrupted copper shields extending over their entire width and length in order to reduce EMI interference to and from the catheter 12. These shields are preferably not connected to the transducer elements.

The conduit 32 also defines four smaller lumens 40, and each of the lumens 40 carries a respective steering line 42. In this embodiment, the steering lines 42 are formed in diametrically opposed pairs, and the steering lines 42 within each pair are continuous from the steering mechanism 26 to the proximal portion of the transducer elements 20 (FIG. 1). The steering line makes a reverse curve at this point and is secured in place to the distal end of a short segment 21 of conduit (approximately 1.5 inches in length) that is integral with the main conduit and is of substantially lower hardness than the body of the catheter. As described below, by increasing tension on one steering line while relieving tension on the diametrically opposed steering line, this lower hardness portion will be preferentially compressed and can bend or be steered in either of two transverse planes. As used herein, the term "set of steering lines" means one or more steering lines.

FIG. 3 shows a cross-sectional view of the steering mechanism 26. As shown in FIG. 3, the steering mechanism 26 includes a central shaft 44 that is fixed in place to the proximal portion 46 of the housing 22. This shaft 44 supports at its forward end 48 the catheter 12. The shaft 44 also supports the first and second steering rings 28,30 for rotation about the axis A. Each of the steering rings 28,30 defines an annular shape which is accessible around the complete circumference of the housing 22. The first and second steering rings 28,30 support first and second steering hubs 50,52 respectively. In this embodiment the steering hubs 50, 52 are integrally formed with the steering rings 28,30, respectively, and rotate with them as a unit. Each of the steering rings 28,30 also supports a pair of anchor pins 54 (FIG. 5). Each anchor pin 54 is mounted for rotation in the respective steering ring 28,30, and can be rotated with a conventional screwdriver. A set screw 56 can be used to lock the anchor pin 54 against undesired rotation after it has been properly adjusted (FIG. 3).

Also as shown in FIG. 3, the shaft 44 fixedly supports first and second guides 58,60. Each of the guides in this embodiment is formed as a passageway oriented longitudinally, parallel to the axis A and disposed radially outwardly from and adjacent to the respective steering hub 50,52. FIG. 3 also shows a slot 62 formed in the steering ring 28 and aligned with the guides 60.

Other elements of the steering mechanism 26 shown in FIG. 3 include a brake knob 64 which is mounted for rotation on the shaft 44. Rotation of the brake knob 64 causes pins (not shown) mounted in the knob to slide along a ramp washer 66. The ramp washer is pushed forwardly (distally) and compresses an elastomeric washer 68 against the second steering ring 30. A collar 70 is positioned between the first and second steering rings 28,30. When the brake knob 64 and pins are rotated in the opposite direction, pressure is removed from the washer 68 and the collar 70, and the steering rings 28,30 can be rotated independently of one another to steer the catheter 12 as desired. When it is desired to lock the steering rings 28,30 in position, the brake knob 64 is rotated to press the washer 68 against the steering ring 30. This pressure causes the steering ring 30 to press the collar 70 against the first steering ring 28, thereby immobilizing both steering rings 28, 30.

In FIG. 3 the steering lines 44 have been deleted for clarity. FIG. 4 is a partially exploded perspective view showing the manner in which the steering lines 42 are passed from the catheter 12 via the guides 58. Two of the steering lines 42 that are diametrically opposed in the catheter 12 pass from the guides 58 around opposite sides of the steering hub 50 and are anchored on the respective anchor pins 54 of the steering ring 28 (FIG. 5).

As shown in FIG. 5, the other two of the steering lines 42 pass from the guides 58 through the arcuate slot 62 and the guides 60 to the second steering hub 52. These steering lines 42 wrap around opposite sides of the steering hub 52 and are then anchored to respective ones of the anchor pins 54 on the steering ring 30.

The steering mechanism shown in FIGS. 3–5 allows each diametrically opposed pair of steering lines 42 to be controlled by a respective one of the steering rings 28,30. When the respective steering ring 28,30 is rotated, one of the corresponding pair of steering lines 42 is increased in effective length, and the other is decreased in effective length. This causes the distal end 14 of the catheter 12 to be steered in the respective plane. Because the steering rings 28,30 extend in an uninterrupted fashion around the circumference of the housing 22, the steering rings 28,30 are always accessible to the user, regardless of the rotational position of the housing 22. Because the steering hubs 50,52 rotate around the same axis as the steering rings 28,30, the steering mechanism is relatively simple in construction and operates substantially without play. As best shown in FIG. 4, indicating bumps 80 protrude from the steering rings. When the steering rings are rotated to align the indicating bumps 80 with a slot 82 on the housing 22, the steering mechanism is placed in a neutral position, in which the tip is not deflected. The bumps 80 and slot 82 act as physical markers and may be raised, lowered, or asymmetrically shaped with respect to the adjacent surface.

During setup, the anchor pins 54 are rotated to shorten or lengthen the respective steering lines 42. Once properly adjusted, the anchor pins 54 are immobilized against further motion with the set screws 56 (FIG. 3).

In this embodiment the steering lines 42 are preferably formed of a flexible, substantially inextensible polymer such as gel spun polyethylene. Such a stranded polymer is well suited for use in this application because of its excellent flexibility, wear resistance, and resistance to stretching. Since the steering line traverses through guides and around the steering hub, it must be flexible. It must also have enough tensile strength to articulate the tip without breaking. A line with low stretch prevents the steering ring from developing excessive backlash over repeated uses. And the line must be resistant to fraying. Stranded metallic wire and Kevlar® line have been tried but are prone to fraying and breaking after minimal cycling.

FIG. 6 shows a side view of a transducer assembly 100 which incorporates a second preferred embodiment of this invention. The transducer assembly 100 is essentially identical to the transducer assembly 10 described above except that only a single steering ring 102 is provided. The transducer assembly 100 can be steered only in a single plane with the steering ring 102, but this arrangement is suitable for many applications.

FIGS. 7 and 8 are sectional views of a transducer assembly 200 that incorporates a third preferred embodiment of this invention. The transducer assembly 200 includes a catheter 202 which may be identical to the catheter 12 described above, and which houses four steering lines 204.

As best shown in FIG. 7, the transducer assembly 200 includes a housing 206 that supports two annular actuators or steering rings 208,210 for rotation about an axis A which corresponds to the centerline of the catheter 202. Each of the steering rings 208,210 is provided with an internal helical gear 212,214, respectively.

As shown in FIG. 7, the transducer assembly 200 includes first and second steering hubs 216,218, each mounted for rotation about a respective axis oriented transversely to the axis A Each steering hub 216,218 includes a respective outer helical gear 220,222, and the gears 220,222 are in driving engagement with the gears 212,214, respectively.

As before, the steering lines 204 are divided into two pairs, each disposed in diametrically opposed lumens of the catheter 202. The steering lines 204 of each pair are wrapped in opposing directions around and anchored in place to the respective steering hub 216,218. In use, the catheter 202 can be steered in either of two transverse planes by appropriately rotating the steering rings 208,210. Rotation of the steering ring 208,210 causes corresponding rotation of the respective steering hub 216,218. As before, rotation of the steering hub 216,218 increases the effective length of one steering line and decreases the effective length of the other steering line in the respective pair in order to steer the distal end of the catheter 202.

Because of the mechanical advantage between the steering rings, 208 and 210, and the steering hubs 220 and 222, generated by the design of the helical surfaces, and because of the friction between the steering rings and the hubs, and between the steering rings and the housing 206, the catheter will retain its adjusted configuration, even when the operator removes his hands from the steering rings. The retention of an adjusted configuration without operator attention is a desirable feature of this design.

Simply by way of example, the following materials can be used with this invention. The steering lines 42, 204 can be formed of a stranded polymer such as that sold under the tradename Spectra® in a thickness of about 0.006 inch. For example the material sold by Cabella's as Spiderwire™.(6# test diameter, 30# test strength) has been found suitable. In addition, the catheter may be formed as described in U.S. patent application Ser. No. 08/791,598, and the flexible circuits of the catheter may be fabricated as described in U.S. patent application Ser. No. 08/791,601, both assigned to the assignee of the present invention. The entire disclosures of both of these patent applications are hereby incorporated by reference.

FIG. 9 shows a perspective view of a transducer assembly 310 as shown and described in above-referenced U.S. patent application Ser. No. 08/791,598. The transducer assembly 310 includes a catheter 312 which defines a distal end 314. In this embodiment the proximal end (not shown) is spaced from the distal end by about 110 centimeters, and the catheter 312 is circular in cross section and defines a maximum cross-sectional dimension of about 3.3 mm.

The distal end 314 of the catheter 312 carries a linear array 316 of transducer elements 318. The transducer elements 318 define an azimuthal axis which is denominated the X axis in FIG. 9, and is parallel to the longitudinal axis of the catheter 312.

Figure 10:
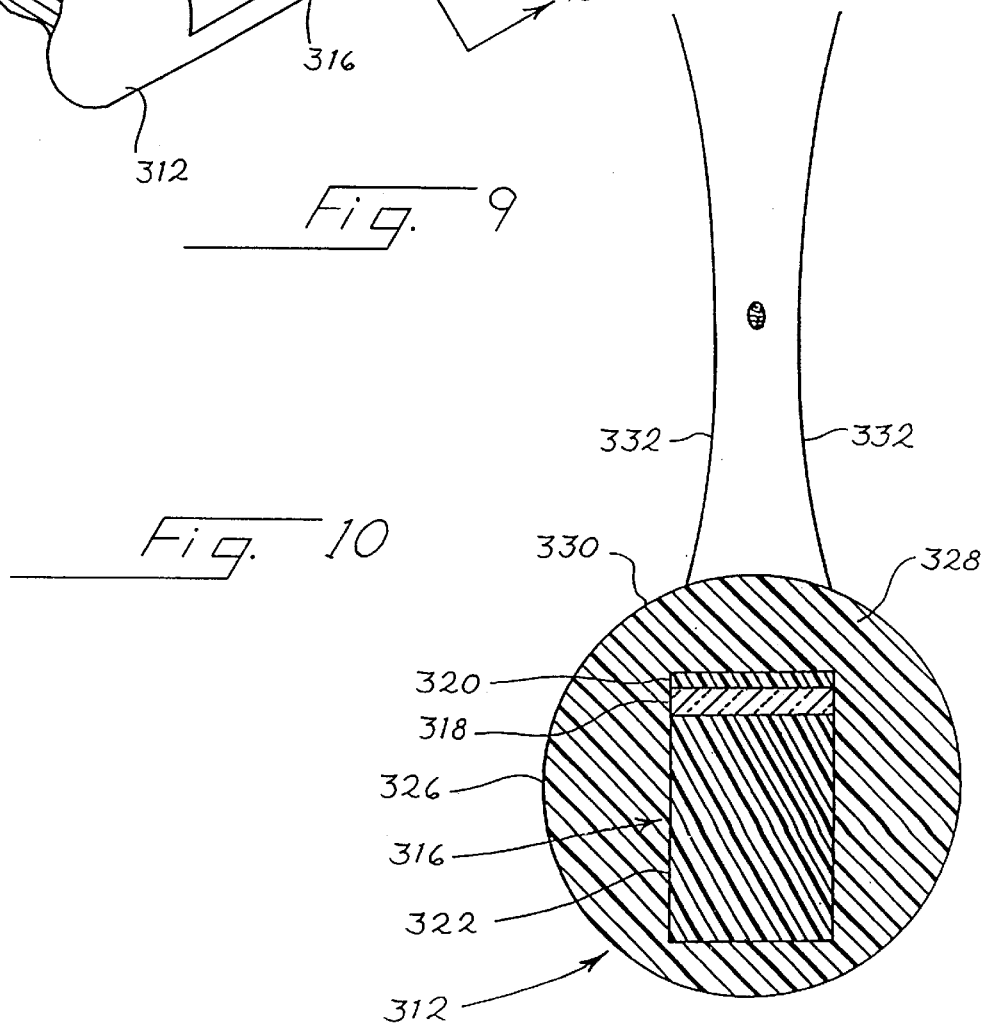
FIG. 10 is a cross-sectional view taken along line 10—10 of FIG. 9.

As shown in FIG. 10, the transducer array 316 includes a matching layer 320 adjacent the active surface of the transducer elements 318, and a backing layer 322 on the reverse side of the transducer elements 318. Flexible circuits are disposed in a lumen defined by the catheter 312 to carry transmit signals and receive signals between the individual transducer elements 318 and an ultrasonic diagnostic imaging system (not shown).

As shown in FIGS. 9 and 10, the catheter 312 includes an end portion 326 that is secured to the tube of the catheter 312 and surrounds the transducer array 316. The part of the end portion 326 that overlies the active surface of the transducer elements 318 forms an acoustic window 328. Typically, the end portion 326 and the acoustic window 328 may be formed of the same material, though this is not required. In this embodiment the end portion 326 is circular in cross section, and the radially outer surface 330 of the acoustic window 328 defines a radius of curvature which is substantially equal to one-half of the maximum cross-sectional dimension of the end portion 326. Since the end portion 326 is circular in cross section in this embodiment, the radius of curvature of the surface 330 is equal to the radius of curvature of the remaining parts of the end portion 326. This arrangement simplifies fabrication of the transducer assembly 310, because it eliminates both the need for a complex shape for the window, and the need for accurate registration between the transducer and the window.

Preferably the maximum cross-sectional dimension of the end portion 326 and the catheter 312 is less than 8 mm. This dimension is more preferably less than 3.3 mm, and most preferably less than 2 mm.

From the foregoing, it should be apparent that several embodiments have been described of steering mechanisms that utilize a steering ring that rotates around the longitudinal axis of the proximal end of the catheter. In each case the steering mechanism converts angular displacement of the steering ring into linear displacement of the steering lines that run the length of the catheter from the proximal to the distal end. Because the steering rings extend completely around the housing, they remain accessible to the user, regardless of the rotational position of the housing. Also, an improved material for steering lines has been disclosed which provides excellent operating characteristics.

Of course, it should be understood that a wide range of changes and modifications can be made to the preferred embodiments described above. For example, the steering line of this invention may be used with any suitable type of steering mechanism. In addition, other steering lines (stranded or unstranded, using other materials such as metal and other polymers) are also possible, and a steering line may be formed by joining two or more sections of differing materials by tying or bonding. For example, a steering line can comprise a gel spun polyethylene section jointed to a Kevlar® section, or a gel spun polyethylene section jointed to a stranded metallic wire section. Additionally, other gear arrangements can be used in the steering mechanism. It should be clearly understood that the foregoing detailed description has described only a few of the many forms that the present invention can take. It is only the following claims, including all equivalents, that are intended to define the scope of this invention.

What is claimed is:

1. An ultrasonic transducer comprising:
    an elongated catheter comprising a distal end portion and a proximal end portion, wherein the maximum cross-sectional dimension of the distal end portion is less than 8 mm;
    a phased array of ultrasonic transducer elements carried by the catheter adjacent the distal end portion, said phased array firing asymmetrically with respect to a longitudinal axis of the catheter adjacent the distal end portion;
    a first set of steering lines carried by the catheter and coupled to the catheter near the distal end portion, said first set of steering lines effective to steer the distal end portion in a first plane; and
    a second set of steering lines carried by the catheter and coupled to the catheter near the distal end portion, said second set of steering lines effective to steer the distal end in a second plane, different than the first plane.

2. The invention of claim 1 wherein said array comprises an azimuthal axis oriented substantially parallel to the longitudinal axis of the catheter adjacent the distal end portion.

3. The invention of claim 1 wherein the first plane is substantially transverse to the second plane.

4. The invention of claim 1 wherein the maximum cross-sectional dimension of the distal end portion is less than 3.3 mm.

5. The invention of claim 1 wherein the maximum cross-sectional dimension of the distal end portion is less than 2 mm.

6. The invention of claim 1 wherein the array comprises a phased linear array.

7. The invention of claim 1 wherein the array comprises a curved linear array.

8. The invention of claim 1 further comprising:

a housing defining a second longitudinal axis extending generally parallel to the proximal end portion of the catheter;

an actuator mounted to the housing for rotation about the second longitudinal axis of the housing;

a steering hub mounted for rotation in the housing and coupled to the actuator such that rotation of the actuator with respect to the housing about the second longitudinal axis causes rotation of the steering hub;

said first set of steering lines secured adjacent the steering hub such that rotation of the steering hub alters effective length of the first set of steering lines to steer the distal end portion in the first plane.

9. The invention of claim 8 further comprising:

a second actuator mounted to the housing for rotation about the second longitudinal axis of the housing;

a second steering hub mounted for rotation in the housing and coupled to the second actuator such that rotation of the second actuator with respect to the housing about the second longitudinal axis causes rotation of the second steering hub;

said second set of steering lines secured adjacent the second steering hub such that rotation of the second steering hub alters effective length of the second set of steering lines to steer the distal end portion in the second plane.

* * * * *